United States Patent [19]
Pier et al.

[11] Patent Number: 5,695,502
[45] Date of Patent: Dec. 9, 1997

[54] SURGICAL CLIP APPLICATOR

[75] Inventors: Arnold Pier, Heinsberg; Jorg Hummen, Monchengladbach, both of Germany

[73] Assignee: United States Surgical Corporation, Norwalk, Conn.

[21] Appl. No.: 515,341

[22] Filed: Aug. 15, 1995

[30] Foreign Application Priority Data

Sep. 29, 1994 [DE] Germany .................. 44 34 864.9

[51] Int. Cl.⁶ .................................................. A61B 17/10
[52] U.S. Cl. .......................... 606/143; 606/142; 606/158; 606/219; 128/325; 128/326
[58] Field of Search ..................... 606/142, 143, 606/158, 157, 219; 227/901, 902; 604/93; 128/4, 325, 326

[56] References Cited

U.S. PATENT DOCUMENTS

| | | |
|---|---|---|
| 2,968,041 | 1/1961 | Skold . |
| 3,777,538 | 12/1973 | Weatherly et al. . |
| 4,027,510 | 6/1977 | Hiltebrandt . |
| 4,084,594 | 4/1978 | Mosior . |
| 4,152,920 | 5/1979 | Green . |
| 4,166,466 | 9/1979 | Jarvik . |
| 4,226,242 | 10/1980 | Jarvik . |
| 4,242,902 | 1/1981 | Green . |
| 4,296,751 | 10/1981 | Blake, III et al. . |
| 4,316,468 | 2/1982 | Klieman et al. .................. 128/325 |
| 4,425,915 | 1/1984 | Ivanov . |
| 4,430,997 | 2/1984 | DiGiovanni et al. . |
| 4,509,518 | 4/1985 | McGarry et al. . |
| 4,534,351 | 8/1985 | Rothfuss et al. . |
| 4,562,839 | 1/1986 | Blake, III et al. . |
| 4,576,166 | 3/1986 | Montgomery et al. . |
| 4,598,711 | 7/1986 | Deniega . |
| 4,646,740 | 3/1987 | Peters et al. . |
| 4,712,549 | 12/1987 | Peters et al. ..................... 128/325 |
| 4,850,355 | 7/1989 | Brooks et al. . |
| 5,030,226 | 7/1991 | Green et al. ..................... 606/158 |
| 5,049,152 | 9/1991 | Simon et al. . |
| 5,084,057 | 1/1992 | Green et al. . |
| 5,100,420 | 3/1992 | Green et al. . |
| 5,104,395 | 4/1992 | Thornton et al. ................ 606/143 |
| 5,112,343 | 5/1992 | Thornton ......................... 606/143 |
| 5,171,247 | 12/1992 | Hughett et al. ................... 606/142 |
| 5,171,249 | 12/1992 | Stefanchik et al. . |

FOREIGN PATENT DOCUMENTS

| | | |
|---|---|---|
| 605254 | 7/1994 | European Pat. Off. . |
| 612505 | 8/1994 | European Pat. Off. . |
| 0671148 | 9/1995 | European Pat. Off. . |
| 9413296 U | 11/1994 | Germany . |

*Primary Examiner*—Michael Powell Buiz
*Assistant Examiner*—Kevin Truong

[57] ABSTRACT

A surgical clip applicator (1) having a handle (2) with an operating device (4) and a shaft tube (6) mounted to the handle (2) is disclosed in which is arranged a connecting rod (8) longitudinally displaceable by the operating device (4) and restorable by spring tension, a clip magazine (12) containing several clips (10) and receivable in the shaft tube (6), and a jaw member (14) for closing the clips (10) at the distal and (16) of the shaft tube (6).

16 Claims, 4 Drawing Sheets

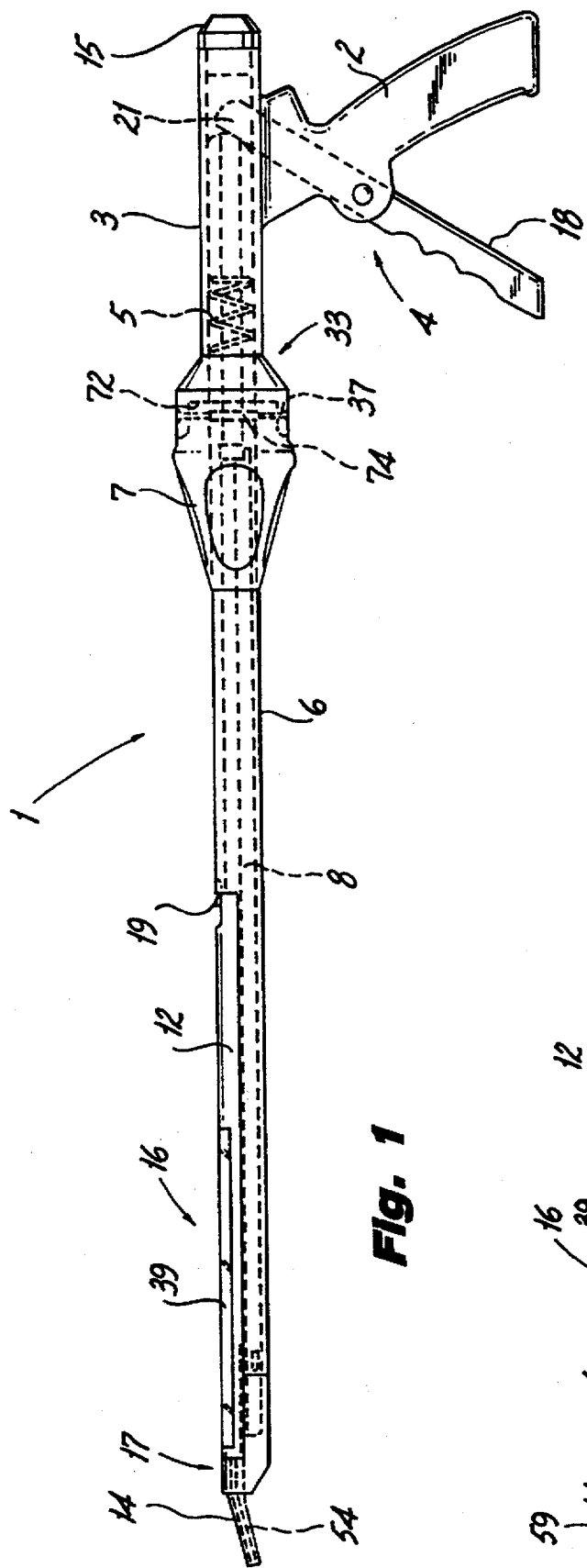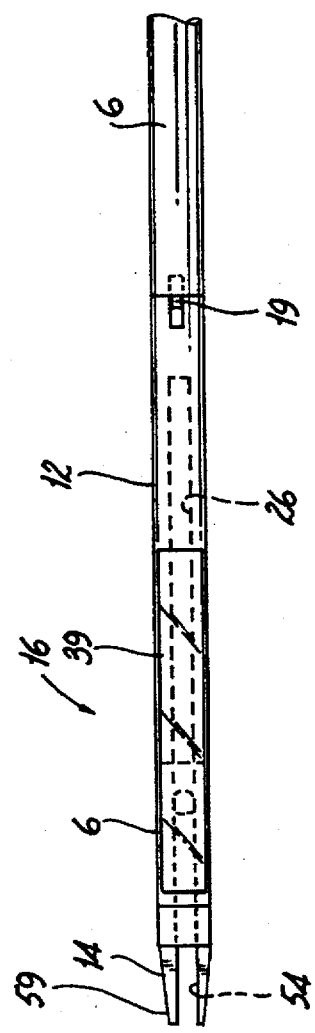

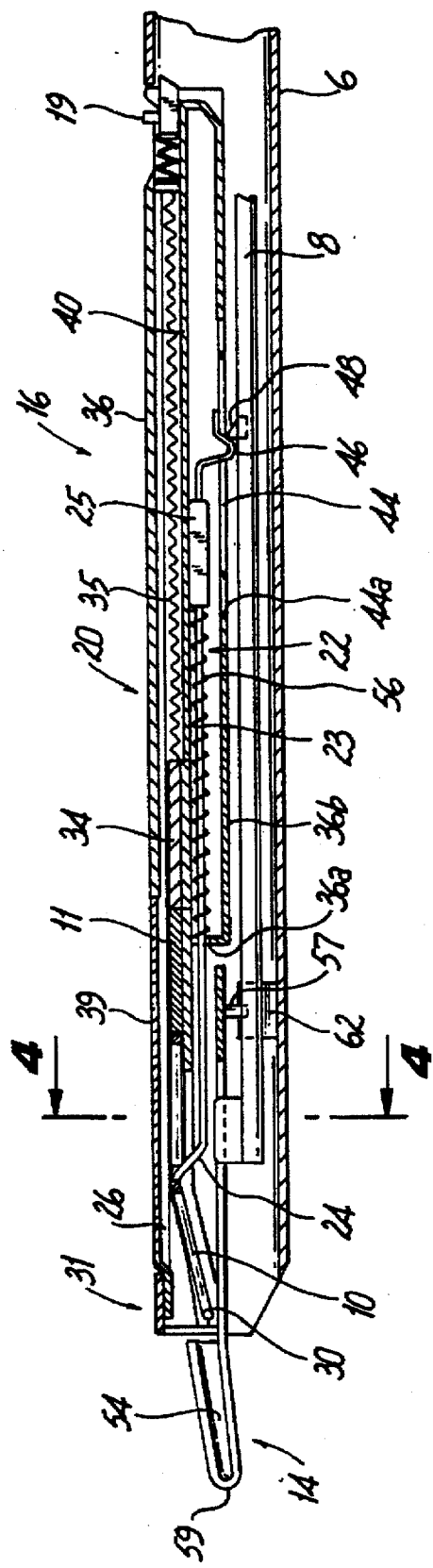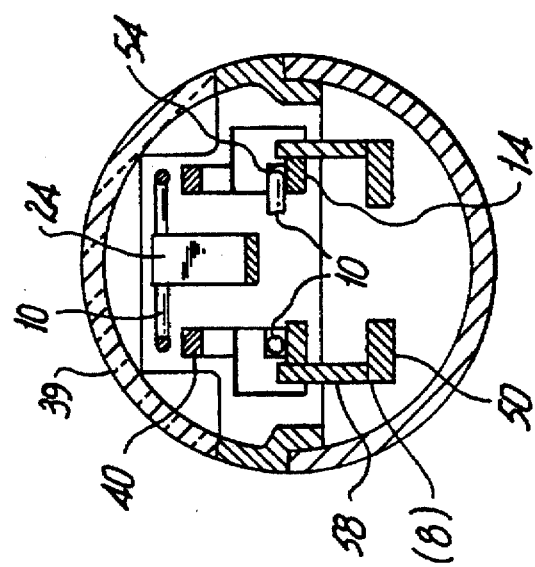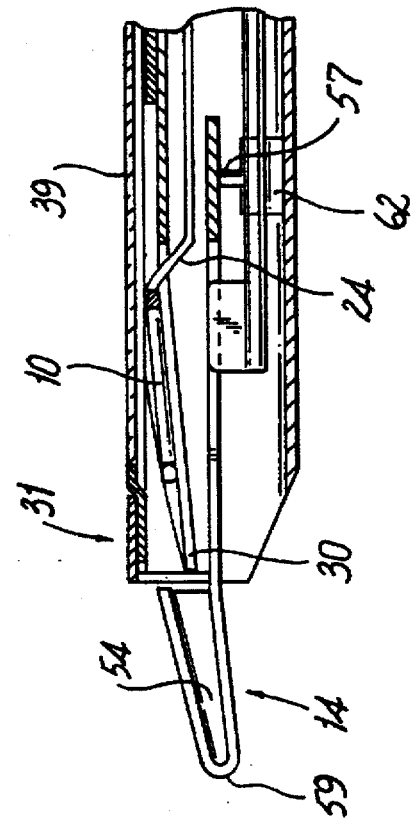

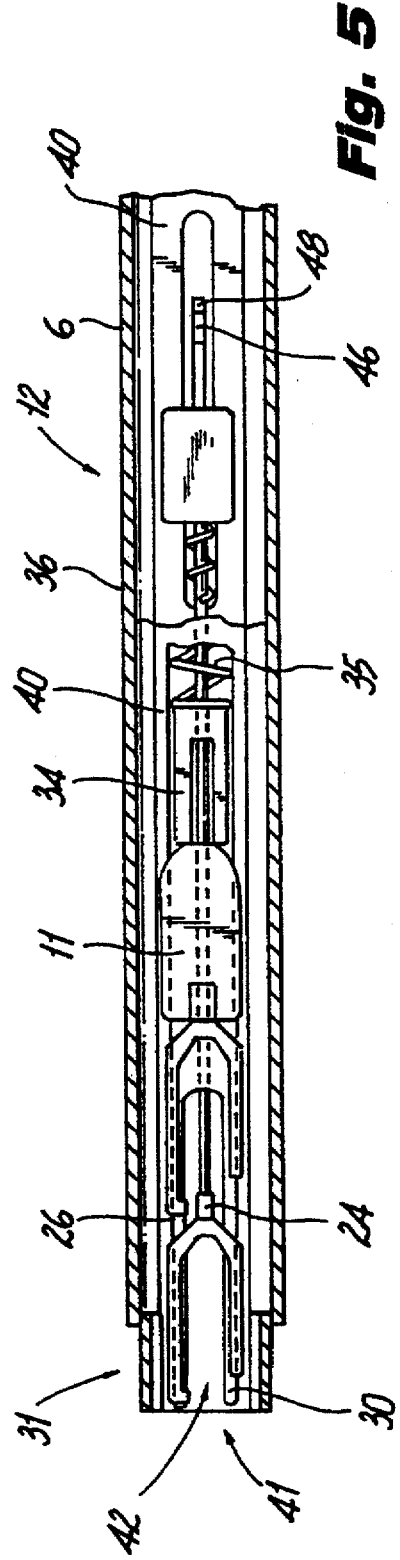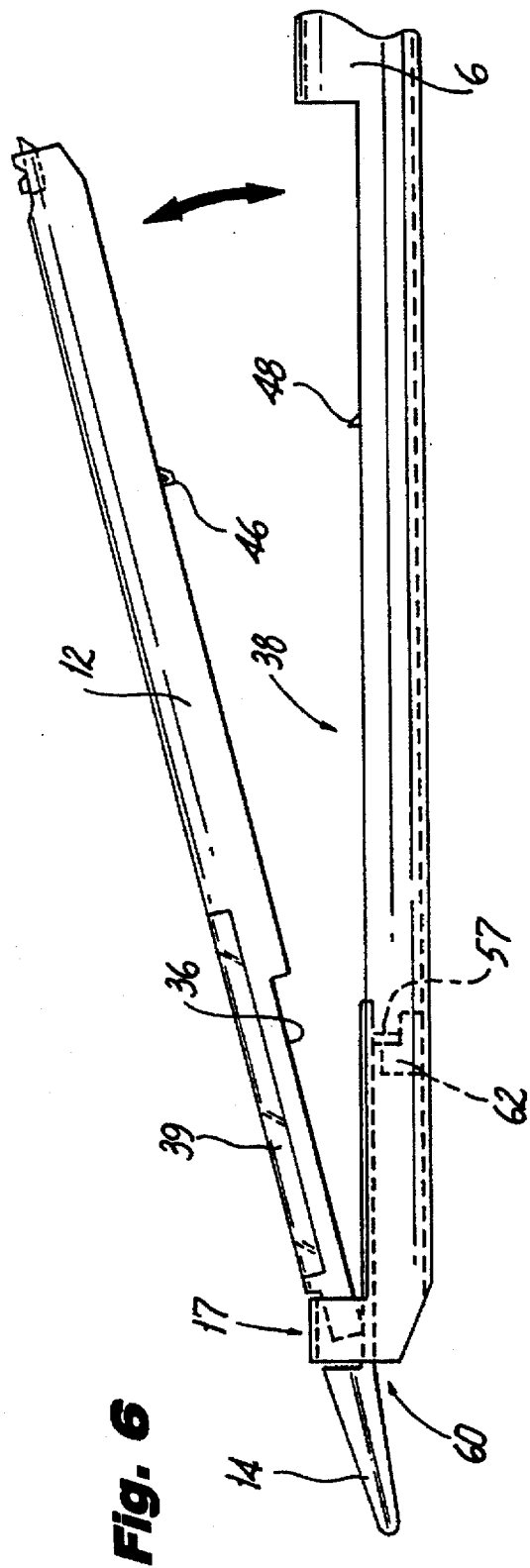

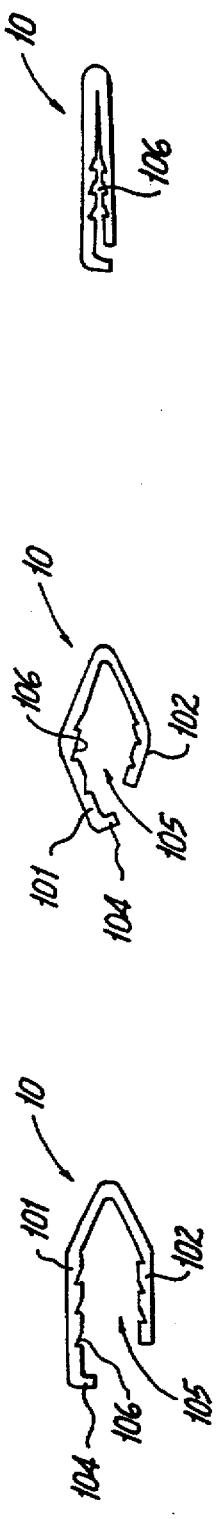
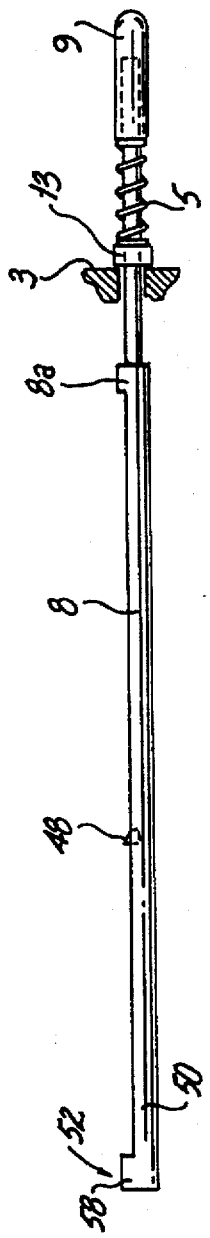
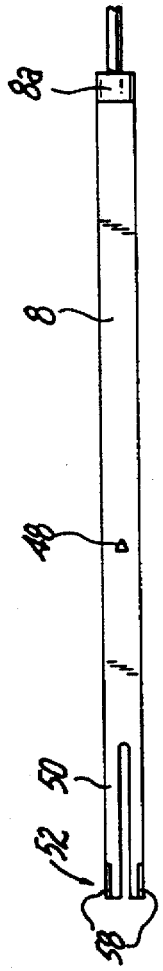
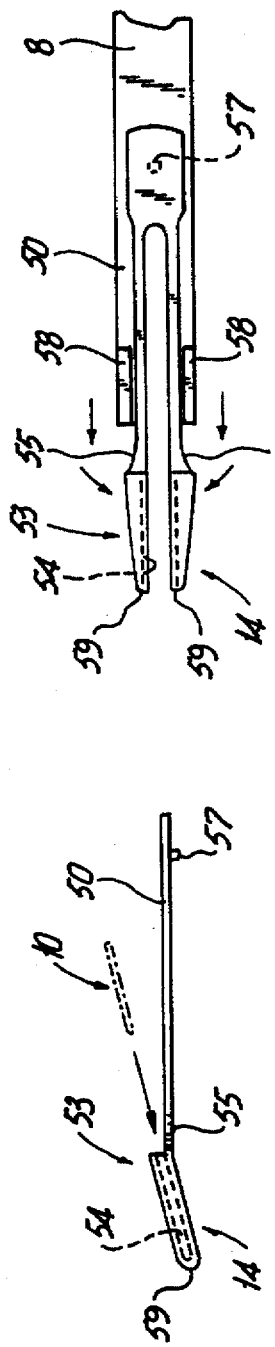
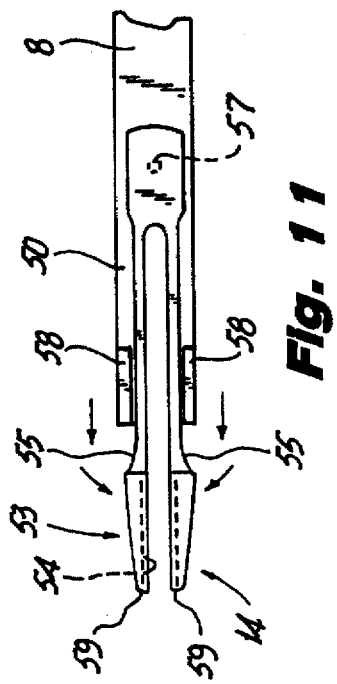

SURGICAL CLIP APPLICATOR

BACKGROUND

1. Technical Field

A surgical clip applicator is provided which is adapted for use in laparoscopic surgery as well as open surgery, and more particularly to a clip applicator including a replaceable unit containing a supply of surgical clips.

2. Description of Related Art

In the case of laparoscopic or endoscopic surgery, a clip applicator is generally introduced through a trocar cannula, e.g. into the abdominal region. Known endoscopic clip appliers for applying multiple clips during a single body entry are described, for example, in U.S. Pat. Nos. 5,084,057 and 5,100,420 to Green et al. In these clip applicators, several clips may be successively supplied from a clip storage unit to a pair of flexible opposing jaws located at the distal end of an endoscopic shaft. Clip application is achieved by the surgeon through manipulation of actuating members associated with the instrument frame. A clip pusher is longitudinally displaceable through the endoscopic shaft to advance a clip to the jaws and a cam channel is also longitudinally displaceable through the endoscopic shaft to close the jaws, thereby forming the clip. Endoscopic clip appliers are also known for applying a single clip during an entry into the body cavity. Such "single clip" clip applicators require withdrawal from the body cavity a new clip into the instrument jaws in order to clinically a second or subsequent clip. "Single clip" clip applicators are generally fabricated from stainless steel and are resterilized for use in subsequent surgical procedures, i.e., such clip applicators are "reusable."

One possible disadvantage of known endoscopic clip applicators which are adapted to advance and form multiple clips in a single insertion into the body cavity is that, as a result of the complicated internal structure(s), they cannot be effectively resterilized. Conversely, "single clip" clip applicators are not capable of placing multiple clips during a single entry into a body cavity. Therefore, known endoscopic clip applicators do not provide an optimal combination of features, i.e., being usable in a repeated manner from surgical procedure to surgical procedure and being capable of placing multiple clips during a single entry into a body cavity.

SUMMARY

It is therefore an object herein to provide a resterilizable, surgical clip applicator which is adapted to advance and form multiple clips during a single insertion into the body cavity.

In addressing such object, a resterilizable clip applicator is provided which is adapted to receive and cooperate with an interchangeable clip magazine so as to advance and form multiple clips during a single entry into a body cavity. The resterilizable clip applicator and the interchangeable clip magazine described herein are capable of use in both endoscopic/laparoscopic procedures and in open procedures.

In a preferred embodiment, with the exception of the connecting rod drive, each interchangeable clip magazine contains all the mechanical elements for the individual transfer of clips to the jaws and subsequent closure of the jaws to form a clip positioned therein. Thus, in the absence of a clip magazine, the clip applicator includes very few mechanical parts, thereby greatly facilitating sterilization and maintenance of the clip applicator, while also reducing the cost thereof. A used clip magazine can be removed and disposed of during a surgical procedure and a fresh clip magazine substituted if additional clips are needed. Additionally, at the conclusion of a procedure, the clip magazine present in the clip applicator may be removed and disposed of and, following sterilization of the clip applicator, a new, sterile clip magazine may be inserted so that the clip applicator can again be used in a new surgical procedure.

As described herein, elements not ideally suited for repeated resterilization and/or long-term maintenance are advantageously housed in the disposable clip magazine. As it is only necessary to dispose of the clip magazine and not the entire clip applicator upon completion of a surgical procedure, a cost saving may be possible as compared to the use of fully disposable clip applicators, and particularly fully disposable endoscopic clip applicators.

In a preferred clip magazine, several successively arranged clips are contained within and guided through a clip housing. The clip magazine contains a number of clips, e.g., ten which may be adequate for a surgical procedure. However, as noted above, if the number of clips is not adequate for the procedure, it is possible to replace an empty clip magazine by a new one during the procedure.

A pair of flexible jaws extend from the distal end of the clip housing and are preferably inclined relative to the longitudinal axis thereof. This inclined orientation of the jaws is advantageous for clip positioning and viewing clip placement.

The clip applicator preferably includes a stationary handle and a movable release lever mounted with respect thereto which cooperate with a connecting rod. Actuation of the release lever by the user advances the connecting rod distally, thereby advancing a single clip through the clip magazine to the jaws. Upon additional distal movement of the release lever, closure of the jaws is effectuated, thereby forming the clip positioned therein.

The clip magazine and/or the operating device preferably includes a locking mechanism which only allows the proximal return of the connecting rod when the operating process or sequence is completed. This ensures that each operating process must be at an end before the connecting rod returns to its starting position.

As the connecting rod moves distally, it first contacts a loading member positioned in the clip magazine for advancing a clip and then, after a clip has been supplied to the jaws, the connecting rod causes the jaws to be cammed closed. The clip loading member within the magazine preferably defines a rod-like reloader which is advanced by the connecting rod. The rod-like reloader preferably defines or cooperates with a clip gripper at its distal end which contacts and advances the furthest forward or distal-most clip in the clip magazine to the jaws. For example, the reloader may be fabricated from a thin metal sheet that, through a curved design at its distal end, forms a clip gripper. Thus, during distal movement of the reloader/clip gripper which results from distal movement of the connecting rod, the clip gripper engages the proximal face of the distal-most clip in the magazine and slides it forward into the jaws.

Preferably, the clip magazine includes at or adjacent to its distal end a resilient stop which is adapted to releasably engage the distal-most clip. Upon distal movement of the reloader in response to actuation of the release lever and resultant distal movement of the connecting rod, the resilient stop deflects and releases the distal-most clip. Behind the proximal-most clip in the clip magazine is preferably positioned a spring-biased slide that acts on and biases the last clip, and therefore the entire array of clips, distally toward the jaws. The spring-biased slide thus provides a force which biases the distal-most clip into engagement with the resilient stop. In place of the final clip in the clip magazine, it is also possible to insert a blocking plate which prevents operation of the jaws in the absence of a clip, e.g., when the clip magazine is empty of clips.

The clip magazine preferably has a substantially semicircular cross-section which is insertable into a tube portion of the clip applicator which also has a substantially semicircular cross-section. Together, the tube portion and the clip magazine form a substantially circular cross-section which corresponds in diameter to the tube portion of the clip applicator proximal of the region which accepts the clip magazine. Thus, the clip magazine does not lead to an increase in the tube diameter and clip applicators with a tube diameter of 10 to 15 mm can be produced, such diameters being readily utilized in conjunction with conventional trocar cannulas. An inspection window may be provided at least in the vicinity of the distal end of the clip magazine so as to facilitate assessment during an operation of the number of clips remaining in the clip magazine.

In a preferred embodiment of the resilient stop, a partition is preferably provided which extends substantially over the entire length of the clip magazine so as to form the bottom of the clip magazine and also to provide a guide surface for the reloading member which extends therebelow. In addition, the distal end of the partition provides a resilient stop for releasably preventing the distal-most clip from moving out of the clip magazine. The partition is preferably forked at its distal end so as to allow the passage of the clip gripper and to form a resiliently deflectable end. Whilst the distal end of the clip magazine is bent downwards, the deflectable end of the partition is aligned with the longitudinal axis of the clip magazine and consequently extends across the opening through which the clips must pass to reach the jaws. The spring tension of the forked partition end is preferably higher than that of the spring-biased slide at the proximal end of the clip shaft.

On the side which is adapted to abut the clip applicator, a coupling member preferably projects from the reloader in the clip magazine which is adapted to engage a corresponding projection on the connecting rod. Upon actuation of the release lever, the connecting rod is moved distally so that the cooperating projections facilitate advancement of a clip into the jaws. The distal movement of the reloader is preferably limited by a stop in the clip magazine, so that the resilient coupling member which extends from the clip magazine is disengaged from the cooperating projection on the connecting rod. With the aid of a restoring spring, the reloader and clip gripper spring back into their respective starting positions behind the furthest forward clip which has moved up in the meantime and which is located adjacent the resilient stop. In response to further actuation of the release lever, a forked guide part at the distal end of the connecting rod is moved forwards and acts on the guide faces of the jaws to close the jaws, thereby forming the clip located therein.

The shaft tube of the clip applicator is preferably mounted in a rotary manner relative to the handle so as to permit repositioning of the jaws for optimal clip application. The jaws are typically inclined with respect to the longitudinal axis of the shaft tube by approximately 15° to 20°, preferably 18°. The inclination of the jaws facilitates positioning of the jaws for clip placement during an operation. A preferred clip for use with the clip applicator/magazine combination is shaped in a substantially symmetrical, pointed, two-wing manner. On one wing projects a shoulder constituting a stop for the other wing. However, use of the clip applicator and/or the clip magazine described herein is not limited to the use of such preferred clips; rather, any hemostatic clip may be advantageously employed with the clip applicator and clip magazine described herein.

BRIEF DESCRIPTION OF THE DRAWINGS

The clip applicator and clip magazine are described in greater detail hereinafter relative to a non-limitative embodiment and the attached drawings, wherein:

FIG. 1 shows a side view of a clip applicator.

FIG. 2 shows a plan view of the distal region of the shaft tube of the clip applicator.

FIG. 3A shows a cross-section through the distal region of the shaft tube.

FIG. 3B shows a clip applicator upon reloading of the distal-most clip.

FIG. 4 shows a cross-section along line IV—IV in FIG. 3A.

FIG. 5 shows a cross-section through the distal region of the shaft tube above the plane of the clips.

FIG. 6 shows insertion of a clip magazine into the shaft tube of a clip applicator.

FIGS. 7a, 7b and 7c show three phases in the process of clip formation.

FIG. 8 shows a connecting rod of the clip applicator in side view.

FIG. 9 shows the connecting rod in plan view.

FIG. 10 shows jaws in side view.

FIG. 11 shows the jaws in plan view with the connecting rod closing the jaws.

DETAILED DESCRIPTION OF PREFERRED EMBODIMENT(S)

Clip applicator 1 shown in FIG. 1, which contains clip magazine 12, has stationary handle 2, to which is movably mounted release lever 18. Release lever 18 cooperates with connecting rod 8 that extends along the longitudinal axis and into shaft tube 6 of clip applicator 1. Through actuation of release lever 18, i.e., pivotal movement of release lever 18 toward stationary handle 2, connecting rod 8 may be moved in the direction of distal end 16 of clip applicator 1. At the end of the operating process connecting rod 8 is returned to its starting position under the bias of restoring spring 5.

Shaft tube 6 is mounted in rotary manner in casing 3 of handle 2 and can be rotated with the aid of gripping ring 7. Rotation of shaft tube 6 also rotates connecting rod which has a rotationally symmetrical design at its proximal end. In its distal region, shaft tube 6 is adapted to receive replaceable clip magazine 12 in recess 38. Clip magazine 12 is inserted so as to hook under a shoulder or like structure at distal end 17 of shaft tube 6 and is locked in shaft tube 6 at the proximal end of recess 38 with the aid of spring-operated pawl 19. Distal end 17 of shaft tube 6 also receives jaw member 14, which is mounted in a removable, but position-fixed, manner relative to shaft tube 6.

Distal movement of connecting rod 8 acts on the one hand on replaceable clip magazine 12, so that single clip 10 can be removed therefrom and supplied to jaws 14, and on the other hand on said jaws 14 so that after positioning of a single clip 10 therewithin, jaws 14 can be closed and clip formation completed. A locking or ratchet mechanism (not shown) may be provided so that return of connecting rod 8 to its initial proximal position is possible only when the operating process is complete, i.e. when release lever 18 has been fully cycled.

Shaft tube 6 is connected in a non-rotary manner, i.e., fixed manner, to gripping ring 7 and, via the latter, is coupled to casing 3. Annular groove 74 is provided on the proximal projection connecting piece 72 of gripping ring 7. A widened sleeve portion of casing 3 engages over connecting piece 72 and receives screw(s) 37, whose end radically engages and rides within annular groove 74. For this purpose the end(s) of screw(s) 37 can be provided with rotary ball bearings.

Connecting rod 8 is of a circular cross-section and passes from shaft tube 6 through gripping ring 7 into casing 3. At its proximal end, connecting rod 8 has plunger 9 which is adapted to strike against lever arm 21 of release lever 18 in casing 3. Restoring spring 5 is a helical spring, which surrounds the proximal end of connecting rod 8 and which with its one end engages against the face of plunger 9 opposite the end which contacts lever arm 21. Restoring spring 5 is supported at its other end against disk ring 13 and is displaceable on, i.e., movable with respect to, connecting rod 8 which is in turn supported against, i.e., abuts, casing 3. Plunger 9 is removably fixed, e.g., screwed, onto the proximal end of connecting rod 8.

Clip applicator 1 can be completely disassembled, e.g., for cleaning, with minimal effort. As stated hereinbefore, clip magazine 12 and the jaw member 14 can be removed from shaft tube 6. After loosening screw(s) 37, shaft tube 6 can be separated from casing 3. Screw-in cap 15 closes the proximal end of casing 3. Following the removal of cap 15, connecting rod 8 can be removed from the casing 3.

Clip applicator 1 is preferably made from metal, with the exception of clip magazine 12. Clip magazine 12 is preferably made from plastic and is a non-resterilizable, disposable article. Thus, clip applicator 1 can be easily disassembled and reassembled, so that resterilization, aside from clip magazine 12, is possible without problems.

FIG. 2 is a plan view of the distal region of shaft tube 6 with clip magazine 12 positioned therewithin. Inspection window 39 in the distal region of clip magazine 12 permits a visual determination of the number of clips 10 remaining in clip magazine 12.

FIGS. 3A and 3B show in cross-section distal region 16 of shaft tube 6. In cross-section shaft tube 6 has a circular shape with a maximum preferred diameter of 15 mm and, more preferably, 10 mm. Clip magazine 12 is inserted in recess 38 and, with the remaining cross-section of shaft tube 6, gives a circular cross-section in the region of clip magazine 12 of comparable diameter to the remainder of shaft tube 6. Connecting rod 8 extends longitudinally through shaft tube 6 and in distal region 16 passes below clip magazine 12 (in the orientation shown in FIGS. 3A and 3B). Projection 48 on connecting rod 8 (see FIGS. 8 and 9) serves to operate clip reloading mechanism 20 of clip magazine 12, whilst the forked, distal end 52 of connecting rod 8, (see FIG. 9) serves to close jaw member 14 during further forward movement of connecting rod 8, so as to close clip 10 located therein. Thus, distal advance of connecting rod 8 which is effectuated by pivotal movement of release lever 18, initially actuates the clip loading function and, after the introduction of clip 10 into jaw member 14, jaw member 14 is cammed closed, whilst clip reloading mechanism 20 (described hereinbelow) springs back in a spring-operated manner to its starting position.

More particularly and with reference to FIG. 3A, upon moving connecting rod 8 distally, downwardly extending coupling member 46 of clip reloader 22 is engaged by projection 48 and advanced distally. At its distal end reloader 22 has clip gripper 24, which engages behind the proximal end of the furthest forward clip 10 in clip magazine 12. Distal advance of connecting rod 8 transfers the distal-most clip 10 from clip path 26 in clip magazine 12 into a clip guidance path 54 in jaw member 14. Clip path 26 is for this purpose aligned with clip guidance path 54 of jaw member 14.

Coupling member 46 of clip reloader 22 projects through recess or slot 44 formed in the bottom face 36b of casing or housing 36 of clip magazine 12, i.e., below the plane defined by the bottom face 36b, and can consequently be engaged by projection 48 of connecting rod 8. Coupling member 46 is a spring element which, when clip gripper 24 reaches its distal-most position, is resiliently disengaged from its engagement with projection 48 through contact with end 44a of slot 44. In other words, the portion of coupling member 46 that extends through recess 44 is deflected at least into, if not above, the plane of the bottom face 36b of housing 36. Reloader 22 then springs back into its starting position under the bias of compression spring 23 and in said position clip gripper 24 is positioned behind the proximal end of the next clip 10 which automatically indexes forward under the bias of spring 35. Reloader 22 preferably includes connecting rod 56, which is surrounded by compression spring 23. Piston element 25 guides the reloader, compression spring 23 being on the one hand supported on piston element 25 and on the other on wall 36a of casing or housing 36.

As shown in the cross-section of FIG. 3A, casing 36 is divided by partition 40 and below partition 40 is positioned connecting rod 56 and compression spring 23 of reloading mechanism 20 and above partition 40 is clip path 26 through which clips 10 travel. Toward the proximal end of clip path 26 is located spring-operated slide 34 with compression spring 35, which biases slide 34 against final clip 10 in clip path 26 or blocking plate 11 whose geometry corresponds to the outer contour of clip 10. The pressure of the spring-operated slide 34 is transferred by means of blocking plate 11 or final clip 10 in clip magazine 12 to all clips 10 distal thereof, so that following the loading of clip 10 into jaws 14, the following clip 10 is advanced to a stop or on-deck position. In the stop position of the furthest forward clip 10, clip gripper 24 engages behind the proximal end of said clip 10, so that in a further operating process it inserts the now furthest forward clip into jaw member 14.

The stop position in clip path 26 is defined by partition 40, which has at its distal end a resilient, forked portion 41, which on the one hand allows the passage of clip gripper 24, but on the other prevents the furthest forward clip 10 from dropping out of clip path 26 or being forced out by spring-operated slide 34. Only on operating clip gripper 24 by means of connecting rod 8 is an adequate force exerted on the resilient portion 41 of partition 40, so that the forked end yields in the downward direction and allows the loading of the furthest forward clip 10 into jaw member 14.

The height and width of clip path 26 are adapted to the dimensions of clips 10. Blocking plate 11 prevents jaw member 14 from closing without a clip 10 positioned therein. In particular, positioning of blocking plate 11 in jaw member 14 prevents any operation of jaw member 14.

FIG. 4 shows a cross-section through shaft tube 6. As noted above, clip path 26 is adapted to the width and height of clips 10 and is downwardly bounded by partition 40. FIG. 5 shows a cross-section through clip magazine 12 in the plane above clip path 26. Clip magazine 12 contains blocking plate 11, which is hollowed out at its distal end in order to prevent a collision with clip gripper 24. FIG. 6 illustrates the insertion of clip magazine 12 in shaft tube 6.

FIGS. 7A, 7B and 7C show the closing of preferred clip 10 as it is closed in three phases. FIG. 7A shows the geometry of clip 10 when located in clip magazine 12. Clip 10 has two substantially parallel wings 101, 102, which have notches 106 on the inner faces 105. One wing 101 is provided with shoulder 104, which projects transversely from said wing 101 and which can serve as a stop for the other wing 102. FIG. 7B shows an intermediate position of clip 10 as it is closed in jaw member 14. FIG. 7C shows the closed clip 10 at the end of the operating process.

FIGS. 8 and 9 show connecting rod 8 in a side view and a plan view. Distal end 52 of connecting rod 8 is forked and has two camming faces 58, which cooperate with inclined guide faces 55 of jaw member 14. As can best be seen from FIG. 11, as connecting rod 8 with its distal end 52 passes below jaw member 14, camming faces 58 engage the guide faces 55 of jaw member 14, so that jaws 59 of jaw member 14 are cammed closed.

At its distal end, which includes clip guidance path 54, jaw member 14 is inclined by approximately 15° to 200°, preferably 18°. Clip guidance path 54 terminates upstream of the distal end of jaws 59, so that a stop position is created for clip 10 inserted in jaw member 14.

In assembling jaw member 14 to the remainder of clip applicator 1, jaw member 14 is inserted into shaft tube 6 through frontal opening 60 and downwardly projecting pin 57 engages receiving aperture 62, as shown in FIG. 3A.

Connecting rod 8 preferably forms a gaseous seal with shaft tube 6 so that insufflatory gases in the body cavity cannot leak through clip applicator 1. Thus, for example, connecting rod 8 may form a disk-like member 8a (see FIGS. 8 and 9) toward its proximal end which, through close tolerance with the inner wall of shaft tube 6, forms a substantial gas seal.

Thus, when fully assembled and ready for use, jaw member 14 initially does not contain a clip 10. As the surgeon pivots release lever 18 toward stationary handle 2, connecting rod 8 is advanced distally through (and relative to) shaft tube 6. Disk 8a forms a gas seal with shaft tube 6 both before and throughout the operation of clip applicator 1.

Projection 48 on connecting rod 8 engages coupling member 46 in clip magazine 12 and advances coupling member 46 distally through recess 44. Distal movement of coupling member 46 translates to distal movement of piston element 25, connecting rod 56 and clip gripper 24, while also compressing spring 23. Clip gripper 24 advances the distal-most clip 10 past the stop defined at the distal end of partition 40 and into jaw member 14. When coupling member 46 reaches the distal end 44a of recess 44, it deflects out of engagement with projection 48 and returns to its proximal-most position under the bias of spring 23, thereby positioning the clip gripper 24 behind the new distal-most clip 10 which will have indexed distally under the bias of spring 35 to the stop position.

Further pivotal movement of release lever 18 advances connecting rod 8 distally such that camming faces 58 engage guide faces 55 on jaws 59, thereby camming jaw member 14 (and clip 10 positioned therewithin) closed. When release lever 18 is released or allowed to return to its original position under the bias of spring 5, connecting rod 8 returns proximally allowing jaws 59 to assume their original spaced configuration and projection 58 to be repositioned behind coupling member 44.

We claim:

1. A surgical clip applicator comprising:
   a handle;
   a shaft tube mounted to the handle and a connecting rod movably positioned within the shaft tube, the connecting rod extending into the handle;
   a clip magazine containing a plurality of clips and a clip reloader, the clip magazine being removably received in the shaft tube; and
   a jaw member positioned at a distal end of the shaft tube
   wherein the connecting rod includes a projection that engages a resilient coupling member which is operatively connected to the clip reloader so that distal movement of the connecting rod may effect distal movement of the clip reloader, and
   further wherein the connecting rod includes at least one camming face at a distal end thereof so that distal movement of the connecting rod may effect camming of the jaw member.

2. The surgical clip applicator of claim 1, wherein the handle includes a release lever operatively connected to the connecting rod.

3. The surgical clip applicator of claim 2, wherein the release lever moves from a non-pivoted position to a pivoted position and, as a result of said movement of said release lever, a clip is advanced from the clip magazine to the jaw member and the jaw member is cammed closed with said advanced clip positioned therewithin.

4. The surgical clip applicator of claim 1, wherein said clip magazine includes a bottom face defining a recess through which at least a portion of the resilient coupling member extends.

5. The surgical clip applicator of claim 4, wherein the recess is bounded by a distal edge and further wherein contact of the resilient coupling member with the distal edge disengages the projection and the resilient coupling member.

6. The surgical clip applicator of claim 1, wherein the clip magazine includes a spring operatively connected to the clip reloader and wherein the spring biases the clip reloader proximally.

7. The surgical clip applicator of claim 1, wherein the clip magazine includes a deflectable stop and wherein the deflectable stop releasably maintains a distal-most clip within the clip magazine.

8. The surgical clip applicator of claim 1, wherein the shaft tube and the clip magazine define a substantially circular cross section.

9. The surgical clip applicator of claim 1, wherein the shaft tube includes a pawl and wherein the pawl releasably maintains the clip magazine in engagement with the shaft tube.

10. The surgical clip applicator of claim 1, wherein the connecting rod includes a disk-like member and wherein the disk-like member cooperates with an inner wall of the shaft tube to form a substantial gas seal.

11. The surgical clip applicator of claim 1, wherein each of the clips includes a pair of wings and one of said pair of wings includes a transverse shoulder.

12. The surgical clip applicator of claim 11, wherein the transverse shoulder acts as a stop for the other of said pair of wings.

13. A clip magazine comprising:
   an elongated housing including a bottom face and an elongated recess having a distal edge formed in the bottom face; a clip reloader movably mounted within the elongated housing;

a resilient coupling member which includes a portion which extends at least in part through the recess and beyond a plane defined by the bottom face; and a plurality of clips positioned within the elongated housing;

wherein contact of the resilient coupling member with the distal edge deflects the portion into the plane of the bottom face.

14. The clip magazine of claim 13, further comprising a spring and wherein the spring biases the clip reloader in a proximal direction.

15. The clip magazine of claim 13, further comprising a stop and wherein the stop releasably maintains a distal-most clip within the elongated housing.

16. A clip applicator comprising:

a handle;

a shaft tube mounted to the handle and a connecting rod movably positioned within the shaft tube, the connecting rod extending into the tube;

a jaw member positioned at a distal end of the shaft tube;

wherein the connecting rod includes a projection at an intermediate point thereof and at least one camming face at a distal end thereof, and further wherein the shaft tube includes a first portion have a substantially circular cross-section and a second portion having a substantially semi-circular cross-section; and further wherein the projection traverses at least in part the semi-circular portion prior to the camming face effecting a camming force on the jaw member.

* * * * *